United States Patent [19]

Matsunaga et al.

[11] Patent Number: 5,420,023
[45] Date of Patent: May 30, 1995

[54] PROCESS FOR PRODUCING L-PHENYLALANINE

[75] Inventors: Tadashi Matsunaga, Fuchu; Takanori Kitamura, Kurashiki, both of Japan

[73] Assignee: Kuraray Co., Ltd., Kurashiki, Japan

[21] Appl. No.: 3,820

[22] Filed: Jan. 11, 1993

Related U.S. Application Data

[63] Continuation of Ser. No. 599,261, Oct. 19, 1990, abandoned, which is a continuation of Ser. No. 904,492, Sep. 8, 1986, abandoned.

[30] Foreign Application Priority Data

Sep. 9, 1985 [JP] Japan ................... 60-199913

[51] Int. Cl.$^6$ ................ C12P 13/22; C12N 11/02
[52] U.S. Cl. .................. 435/108; 435/170; 435/177; 435/872; 435/843; 435/840
[58] Field of Search ............ 435/108, 872, 843, 840, 435/170, 177

[56] References Cited

U.S. PATENT DOCUMENTS

| | | | |
|---|---|---|---|
| 3,183,170 | 5/1965 | Kitai et al. | 435/108 |
| 4,590,161 | 5/1986 | Kula et al. | 435/108 |

FOREIGN PATENT DOCUMENTS

| | | | |
|---|---|---|---|
| 0099517 | 2/1984 | European Pat. Off. | C12P 1/00 |
| 0137646 | 4/1985 | European Pat. Off. | C12P 13/22 |
| 0151488 | 8/1985 | European Pat. Off. | C12P 13/22 |
| 0120208 | 7/1986 | European Pat. Off. | C12N 9/06 |
| 1252911 | 12/1960 | France | 435/108 |
| 2108117 | 5/1972 | France | C12P 13/22 |
| 2217296 | 9/1974 | France | C12P 13/04 |
| 3427495 | 2/1985 | Germany | C07C 101/04 |
| 2084155 | 4/1982 | United Kingdom | C12P 13/04 |

OTHER PUBLICATIONS

ATCC Catalogue of Bacteria, 1992, pp. 270–273.
ATCC Catalogue of Bacteria, 1985, pp. 149–150.
Goodfellow et al, *The Biology of the Actinomycetes,* 1984, Academic Press, pp. 77–79, 89–94 and 203.
Wong et al, "Enzyme-Catalyzed Organic Synthesis: NAD(P)H Regeneration Using Dihydrogen and the Hydrogenase from Methanobacterium Thermoautotrophicum", *Journal of the American Chemical Society,* vol. 103, pp. 627–628 (1981).
Tsuji et al, "Microbial Production of L-Phenylalanine", *Chemical Abstracts,* 105:59463t (Mar. 20, 1986).
T. Matsunaga, et al, "Regeneration of NAD(P)H by Immobolized Whole Cells of *Clostridium butyricum* Under Hydrogen High Pressure", *Biotechnology & Bioengineering,* vol. 29, No. 9, Sep. 1985, pp. 1277–1281.
Hilhorst et al, "Enzymatic Conversion of Apolar Compounds in Organic Media Using an NADH-Regenerating System and Dihydrogen as Reductant", FEBS letters, vol. 159, No. 1, 2 (Aug. 1983), pp. 225–228.

*Primary Examiner*—Irene Marx
*Attorney, Agent, or Firm*—Burns, Doane, Swecker & Mathis

[57] ABSTRACT

A process for producing L-phenylalanine at high rates of formation and in good yields is provided which comprises allowing a microorganism which belongs to the genus Nocardia and is capable of producing L-phenylalanine from phenylpyruvic acid or a salt thereof and an amino group donor to act upon an aqueous solution containing phenylpyruvic acid or a salt thereof and an amino group donor selected from the group consisting of ammonium salts and ammonia in a hydrogen gas atmosphere.

14 Claims, No Drawings

PROCESS FOR PRODUCING L-PHENYLALANINE

This application is a continuation of application Ser. No. 07/599,261, filed Oct. 19, 1990, now abandoned, which is a continuation of application Ser. No. 06/904,492, filed Sep. 8, 1986, now abandoned.

BACKGROUND OF THE INVENTION

1. Field of the Invention

This invention relates to a process for producing L-phenylalanine and, more particularly, to a process for producing L-phenylalanine which comprises allowing a microorganism which belongs to the genus Nocardia and is capable of producing L-phenylalanine from phenylpyruvic acid or a salt thereof and an amino group donor to act upon an aqueous solution containing phenylpyruvic acid or a salt thereof and an amino group donor in a hydrogen gas atmosphere.

2. Description of the Related Art

So-far known processes for producing L-phenylalanine from phenylpyruvic acid or a salt thereof and an amino group donor using a microorganism or an enzyme derived therefrom include, among others, (1) processes comprising allowing the culture broth obtained by cultivating a bacterium belonging to the genus Alcaligenes or Pseudomonas, for instance, in a nutrient medium, living or dried cells isolated from such culture broth or phenylpyruvate transaminase obtained from the culture broth of a fungus belonging to the genus Aspergillus, Penicillium or the like to act upon a mixture containing phenylpyruvic acid and an amino group donor such as L-aspartic acid, L-glutamic acid or the like (cf. Japanese Patent Publications Nos. 10672/62 and 20556/70), (2) processes comprising effecting the enzymatic transamination between L-glutamic acid and phenylpyruvic acid by using cultured cells of a bacterium belonging to the genus Escherichia, Proteus or Clostridium, for instance, a sonicate or an extract of said cells, each having enzymatic activities of hydrogenase, L-glutamate dehydrogenase and transaminase, in the presence of a nitrogen source and in a hydrogen gas atmosphere so that L-phenylalanine can be prepared through L-glutamic acid by execution of L-glutamic acid formation and transamination in such manner that the substrate may be conjugative (cf. U.S. Pat. No. 3,183,170 and Japanese Patent Publication No. 1995/65), (3) processes comprising reacting phenylpyruvic acid with ammonia in the presence of a compatible source of reducing equivalents such as glucose and in the presence of the culture of a bacterium belonging to the genus Escherichia or Enterobacter, among others, and capable of producing dehydrogenase and transaminase (cf. European Patent Publication No. 140,503) and (4) processes comprising reacting phenylpyruvic acid with an ammonium ion source such as ammonium chloride in the presence of nicotinamide-adenine dinucleotide and in the presence of L-phenylalanine dehydrogenase obtained from the strain Brevibacterium species DSM2448 (cf. U.S. Pat. No. 4,590,161).

Those microorganisms or enzymes derived therefrom which are actually known to be usable in producing L-phenylalanine from phenylpyruvic acid and an amino group donor have been limited to bacteria or enzymes derived from bacteria or fungi, as mentioned above. It would be desirable if the microorganism to be used in producing L-phenylalanine could be selected from within a broader range of microorganisms.

From such point of view, several reseachers inclusive of one of the present inventors have previously found that L-phenylalanine can be produced by allowing a microorganism belonging to the genus Nocardia which is capable of producing L-phenylalanine from phenylpyruvic acid or a salt thereof and an amino group donor to act upon an aqueous solution containing phenylpyruvic acid or a salt thereof and an amino group donor (cf. Japanese Patent Application Laid-Open No. 56088/86). When this process is used, it is possible to produce L-phenylalanine from phenylpyruvic acid or a salt thereof and a variety of amino group donors in good yields and in a simple and easy manner. Nevertheless, it would be more preferable if L-phenylalanine could be produced more efficiently.

SUMMARY OF THE INVENTION

An object of the invention is to provide a process for producing L-phenylalanine at high rates of formation and in good yields directly from phenylpyruvic acid or a salt thereof and an amino group donor by using microorganisms which have hitherto not reported to be utilizable in the production of L-phenylalanine from phenylpyruvic acid or a salt thereof and an amino group donor. This object as well as other objects and advantages of the present invention will become apparent to those skilled in the art from the following description.

Thus, the invention provides a process for producing L-phenylalanine which comprises allowing a microorganism belonging to the genus Nocardia and capable of producing L-phenylalanine from phenylpyruvic acid or a salt thereof and an amino group donor to act upon an aqueous solution containing phenylpyruvic acid or a salt thereof and an amino group donor selected from the group consisting of ammonium salts and ammonia in a hydrogen gas atmosphere.

DETAILED DESCRIPTION OF THE INVENTION

Representative microorganisms belonging to the genus Nocardia and capable of producing L-phenylalanine from phenylpyruvic acid or a salt thereof and an amino group donor have been deposited at the Fermentation Research Institute, Agency of Industrial Science and Technology, Japan (hereinafter referred to as "FERM") and include the strains *Nocardia opaca* C-8-5 (FERM BP-1119), *Nocardia coeliaca* C-7-5 (FERM BP-1117) and *Nocardia erythropolis* C-6-2 (FERM BP-1118). The bacteriological characteristics of these strains are summarized in Table 1. *Nocardia opaca* C-8-5, *Nocardia erythropolis* C-6-2 and *Nocardia coeliaca* C-7-5 were deposited with the Fermentation Research Institute, Agency of Industrial Science and Technology (FRI), 1-3, Higashi 1 chome, Yatabe-machi, Tsukuba-gun, Ibaraki-ken, 305, Japan as FERM P-7668, FERM P-7667 and FERM P-7666,

TABLE 1

| Bacteriological properties | *Nocardia opaca* C-8-5 | *Nocardia coeliaca* C-7-5 | *Nocardia erythropolis* C-6-2 |
|---|---|---|---|
| Morphological | | | |

TABLE 1-continued

| characteristics | | | | | | | | | |
|---|---|---|---|---|---|---|---|---|---|
| Outline | Mostly rod-shaped (0.8 × 3–5 μ), partly filamentous. | | | Young vegetative growth is mycelial and fragmentation occurs with aging to produce rods (0.7–0.8 × 5–10 μ). | | | Mycelial growth with fragmentation occurring early to produce rods (0.8 × 5–10 μ). | | |
| Color of colonies | Orange on many media | | | White | | | Orange on most media | | |
| Spore | None | | | None | | | None | | |
| Flagellum | None | | | None | | | None | | |
| Gram stain | Positive | | | Positive | | | Positive | | |
| Acid fast stain | Negative | | | Negative | | | Negative | | |
| Cultural characteristics (30° C., 1 week) | Growth | Color of colonies | Diffusible pigment | Growth | Color of colonies | Diffusible pigment | Growth | Color of colonies | Diffusible pigment |
| Sucrose nitrate agar | Poor | White | None | Poor | White | None | Moderate | Orange | None |
| Glucose asparagine agar | Moderate | White | None | None | — | — | Moderate | Orange | None |
| Glycerol asparagine agar | Moderate | White | None | Poor | White | None | Moderate | White | None |
| Starch inorganic salt agar | Poor | Orange | None | Good | White | None | None | — | — |
| Tyrosine agar | Moderate | Orange | None | None | — | — | Good | Orange | None |
| Nutrient agar | Moderate | Orange | None | Good | White | None | Moderate | Orange | None |
| Yeast malt agar | Good | Orange | None | Good | White | None | Good | Orange | None |
| Oatmeal agar | None | — | — | Poor | White | None | None | — | — |
| Bacteriological properties | Nocardia opaca C-8-5 | | | Nocardia coeliaca C-7-5 | | | Nocardia erythropolis C-6-2 | | |
| Physiological characteristics Range for growth | | | | | | | | | |
| Temperature | 37° C. and below (optimally 30° C.) | | | 42° C. and below (optimally 37° C.) | | | 37° C. and below (optimally 30° C.) | | |
| pH | 7–9 | | | 5–9 | | | 5–9 | | |
| Gelatin liquefaction | Negative | | | Positive | | | Negative | | |
| Starch hydrolysis | Negative | | | Positive | | | Negative | | |
| Skim milk coagulation or peptonization | Peptonization under alkaline conditions | | | Coagulation | | | Peptonization under alkaline conditions | | |
| Melanoid pigment production | Negative | | | Negative | | | Negative | | |
| Nitrate reduction | Positive | | | Negative | | | Positive | | |
| Denitrification | Negative | | | Negative | | | Negative | | |
| Methyl red test | Negative | | | Positive | | | Negative | | |
| Voges-Proskauer test | Negative | | | Positive | | | Negative | | |
| Indole production | Negative | | | Negative | | | Negative | | |
| Hydrogen sulfide production | Positive | | | Positive | | | Positive | | |
| Citrate utilization in | | | | | | | | | |
| Koser medium | Positive | | | Positive | | | Positive | | |
| Christensen medium | Positive | | | Positive | | | Positive | | |
| Urease | Positive | | | Negative | | | Positive | | |
| Oxidase | Positive | | | Positive | | | Positive | | |
| Catalase | Positive | | | Positive | | | Positive | | |
| Oxygen requirement | Aerobic | | | Facultatively aerobic | | | Aerobic | | |
| Oxidation/Fermentation test | Negative | | | Fermentative | | | Negative | | |
| Casein hydrolysis | Negative | | | Positive | | | Negative | | |
| Dextrin utilization | Negative | | | Positive | | | Negative | | |
| Gas and acid production from sugars | Acid produced from D-fructose, D-sorbitol and D-mannitol; gas | | | Acid procuced from D-glucose, D-fructose, maltose, sucrose, | | | Acid produced from D-fructose, D-sorbitol, inositol, glycerol and starch; gas not produced | | |

TABLE 1-continued

|  | not produced | trehalose, glycerol and starch; gas not produced |  |
|---|---|---|---|
| Utilization of carbon sources (Note 1) |  |  |  |
| L-Arabinose | − | − | − |
| D-Xylose | − | + | − |
| D-Glucose | ++ | ++ | ++ |
| D-Fructose | ++ | ++ | ++ |
| Sucrose | − | + | + |
| Inositol | − | − | ++ |
| L-Rhamnose | − | + | − |
| Raffinose | − | − | − |
| D-Mannitol | ++ | + | ++ |

(Note 1) The assimilation of each carbon source was determined by cultivation on Pridham-Gottlieb agar medium at 30° C. for 7 days:
− ... No growth; + ... Poor growth; ++ ... Good growth.

The strains *Nocardia opaca* C-8-5, *Nocardia coeliaca* C-7-5 and *Nocardia erythropolis* C-6-2 have been identified on the basis of their bacteriological characteristics given in Table 1. Thus, in view of the morphological findings, such as the findings that all the three strains are rods, that mycelia are formed under certain conditions, that spores are absent, that they have no motility and that they are positive to Gram stain, as well as their physiological characteristics, for example their aerobic character, they have been identified as microorganisms belonging to the genus Nocardia classified under Actinomycetes and related organisms in accordance with Bergey's Manual of Determinative Bacteriology, 8th edition. Furthermore, as for the strain *Nocardia coeliaca* C-7-5, the strain has been identified as a microorganism belonging to the species *Nocardia coeliaca* in accordance with the above manual on the basis of the morphological findings, such as the findings that its colonies have a white color and that its mycelium is long, as well as on the physiological characteristics such as the lack of ability to liquefy gelatin or reduce nitrates. Regarding the strains *Nocardia erythropolis* C-6-2 and Nocardia opaca C-8-5, they have been identified as microorganisms belonging to the species *Nocardia erythropolis* and *Nocardia opaca*, respectively in accordance with the above manual on ,the basis of their physiological characteristics such as the ability to liquefy gelatin, negative response to the Oxidation/Fermentation test, lack of ability to hydrolyze casein and starch and lack of ability to utilize dextrin as well as their respective morphological characteristics. In identifying the strain *Nocardia erythropolis* C-6-2, the article by I. Komura et al. appearing in The Journal of General and Applied Microbiology, vol. 19, pages 161-170 (1973) was helpful.

In the practice of the invention, the above-mentioned microorganisms belonging to the genus Nocardia and capable of producing L-phenylalanine from phenylpyruvic acid or-a salt thereof and an amino group donor are cultivated in a nutrient medium, and the culture broths, living cells separated from said broths or dried cells derived therefrom are used. The cultivation of such microorganisms is carried out in the same manner as in the cultivation of microorganisms in general, generally in the manner of shake culture or submerged culture with aeration and agitation, using a liquid medium. As the nutrient medium, any medium containing nutrient sources utilizable by the above microorganisms can be used. Usable carbon sources are, for example, glucose, sucrose, maltose, peptone, meat extract, yeast extract, corn steep liquor and glycerol. These are used either alone or in combination, generally in a concentration of about 0.1-5% by weight. Usable nitrogen sources are such inorganic nitrogen sources as ammonium nitrate, ammonium sulfate and ammonium chloride and such organic nitrogen sources as peptone, meat extract, yeast extract and corn steep liquor. In addition, inorganic salts such as dipotassium hydrogen phosphate, potassium dihydrogen phosphate, magnesium sulfate and sodium chloride may be added. For enhancing the ability of the above-mentioned microorganisms to produce L-phenylalanine, it is preferable to add phenylalanine, a phenylalanine ester, such as phenylalanine methyl ester, phenylalanine amide or the like, each in L or D form or as a mixture of L and D forms, or phenylpyruvic acid or the like to the medium in a concentration of about 0.1-1% by weight. Particularly, the use of phenylalanine gives better results. The cultivation conditions are not critical. However, the cultivation is carried out in the manner of shake culture or submerged culture with aeration and agitation generally at 25°-37° C., preferably at 28°-35° C., and at a pH of 7-8 for about 4-24 hours. After cultivation, cells can be separated from the culture broth with ease by filtration or centrifugation, for instance. The living cells thus harvested may be dried by a conventional method to give dry cells.

The thus-obtained living or dried cells are preferably immobilized to a support prior to use. The immobilization of the living or dried cells can be performed by a conventional method of immobilizing microorganisms in general, for example by suspending the living or dried cells in water, isotonic sodium chloride solution or a buffer, such as tris buffer, citrate buffer or tricine buffer, admixing a polymerizable monomer or a polymerizable prepolymer with the suspension and allowing the polymerization reaction to proceed or by admixing a polymer with such suspension and coagulating the polymer with the cells. The immobilized living or dried cells can maintain their enzyme activity for a long period of time and can be easily recovered from the reaction mixture for reuse, as mentioned later herein. Examples of the support are polyacrylamide, carrageenan, fibroin, gelatin, collagen, agar, alginic acid salts, diethylaminoethyl-Sephadex, and photocurable resins based on such a prepolymer as polyethylene glycol diacrylate or polypropylene glycol diacrylate. These supports are used in any appropriate form and shape, for example in a granular, filmy or fibrous form. For efficient use of the immobilized cells, it is generally preferable that the support has a large specific surface area. When the ease of forming and handling of the support, among others, is also taken into consideration, the support should preferably be granular, more preferably spherical. When spherical, the support should preferably have an average diameter of about 0.1–10 mm to give favorable results. The immobilized amount of living or dried cells to the support on the dry cell basis is generally about 1–100 grams, preferably about 5–50 grams, per liter of the support. For enhancing the ability of such immobilized cells to produce L-phenylalanine, it is preferable to treat such immobilized cells with an aqueous solution containing phenylalanine, a phenylalanine ester such as phenylalanine methyl ester, phenylalanine amide or the like, each in L or D form or as a mixture of L and D forms, or phenylpyruvic acid or the like. In particular, treatment with an aqueous solution containing phenylalanine gives more favorable results. For example, such treatment is carried out by immersing the immobilized cells in a nutrient medium such as mentioned above or a buffer such as tris buffer, citrate buffer or tricine buffer, each containing phenylalanine, a phenylalanine ester, phenylalanine amide or the like either in L or D form or as a mixture of L and D forms, or phenylpyruvic acid or the like in a concentration of about 0.1–1% by weight generally at 25°–40° C., preferably at 30°–37° C., at a pH of 7–8 for about 2–50 hours.

In accordance with the invention, the desired L-phenylalanine can be obtained by allowing the culture broth mentioned above or living or dried cells separated therefrom to act upon an aqueous solution containing phenylpyruvic acid or a salt thereof and an amino group donor selected from the group consisting of ammonium salts and ammonia in a hydrogen gas atmosphere. The rate of formation of L-phenylalanine increases as the hydrogen gas partial pressure increases. The hydrogen gas partial pressure should preferably be not less than 0.5 atmosphere (absolute), more preferably not less than 10 atmospheres (absolute), still more preferably not less than 20 atmospheres (absolute). From the viewpoint of efficient commercial production of L-phenylalanine, said pressure should preferably be not less than 50 atmospheres (absolute), most preferably not less than 80 atmospheres (absolute). Although there is no particular upper limit to the hydrogen gas partial pressure, an upper limit should be placed on the hydrogen gas partial pressure generally at about 200 atmospheres (absolute), preferably at about 150 atmospheres (absolute), in view of the cost of equipment as required for production apparatus, in particular the pressure-resistant reactor.

As the salt of phenylpyruvic acid to be used in the invention, there may be exemplified an alkali metal salt of phenylpyruvic acid, such as sodium phenylpyruvate, potassium phenylpyruvate, lithium phenylpyruvate or the like; an alkaline earth metal salt of phenylpyruvic acid, such as calcium phenylpyruvate, magnesium phenylpyruvate or the like; ammonium phenylpyruvate; a salt of amine with phenylpyruvic acid, such as triethylammonium phenylpyruvate or the like; and so forth. Phenylpyruvic acid or a salt thereof is used in an amount such that its concentration in the aqueous solution containing phenylpyruvic acid or a salt thereof and an amino group donor amounts to generally about 1–200 millimoles per liter, preferably about 3–100 millimoles per liter, most preferably about 5–80 millimoles per liter.

As the amino group donor to be used in the invention, there may be exemplified an ammonium salt, such as ammonium acetate, ammonium chloride, ammonium nitrate, ammonium sulfate, ammonium carbonate, diammonium hydrogen phosphate or ammonium dihydrogen phosphate, and ammonia. Such amino group donors are used either alone or as a mixture of two or more. The amino group donor is used generally in an amount of about 1–100 moles per mole of phenylpyruvic acid or a salt thereof. The reaction is preferably carried out at a pH of about 6–10. The pH of the reaction system should preferably be within the range of about 7–9, more preferably within the range of about 7.5–8.5. For adjusting the pH of the reaction system, there may be added to the reaction system buffers such as tris buffer, phosphate buffer, citrate buffer and tricine buffer; inorganic acids such as hydrochloric acid, sulfuric acid and phosphoric acid; organic acids such as formic acid, acetic acid, propionic acid and benzenesulfonic acid; alkali metal or alkaline earth metal hydroxides and carbonates such as sodium hydroxide, potassium hydroxide, barium hydroxide, sodium carbonate, potassium carbonate and sodium hydrogen carbonate; ammonia; amines such as triethylamine; and so forth. Among them, buffers are preferred. The reaction temperature is generally in the range of about 20°–50° C., preferably about 30°–40° C. In some instances, the presence of at least one coenzyme selected from the group consisting of nicotinamide-adenine dinucleotide (hereinafter referred to as "NAD") and reduced nicotinamide-adenine dinucleotide (hereinafter referred to as "NADH") in the reaction-system may further increase the rate of formation of L-phenylalanine. The coenzyme is used in a concentration of about 0.1–2.0 millimoles per liter of the aqueous solution in the reaction system.

After completion of the reaction, cells are removed from the reaction mixture by filtration or centrifugation, for instance, and L-phenylalanine accumulated in the reaction mixture can be separated from the filtrate or supernatant by the ion exchange resin method or crystallization method, for instance.

The immobilized cells recovered from the reaction mixture may be reused as desired in the process for producing L-phenylalanine in accordance with the present invention. In case the immobilized cells recovered have a decreased ability to produce L-phenylalanine, the ability to produce L-phenylalanine can be recovered for reuse by treating the immobilized cells with an aqueous solution containing phenylalanine, a phenylalanine ester, phenylalanine amide or the like, either in L or D form or as a mixture of L and D forms, or phenylpyruvic acid or the like in the manner mentioned above.

The product of the process according to the present invention, namely L-phenylalanine, is one of the essential amino acids and is a nutritionally or medicinally important substance. It is also useful as a raw material for the synthesis of α-L-aspartyl-L-phenylalanine methyl ester (aspartame), an artificial sweetener.

The following examples illustrate the present invention in further detail but are not to be construed as limiting the scope thereof.

EXAMPLE 1

Meat extract (1.0 g), 1.0 g of peptone, 0.5 g of sodium chloride and 0.3 g of L-phenylalanine were dissolved in purified water, the pH of the solution was adjusted to 7.2 by addition of 1N aqueous sodium hydroxide and the volume was made 100 ml by further addition of purified water. The thus-obtained medium (hereinafter such medium being referred to as "medium 1") (100 ml)

was placed in a 500-ml Sakaguchi flask and steam-sterilized at 120° C. for 10 minutes. One loopful of the strain *Nocardia opaca* C-8-5 grown on an agar slant medium prepared by adding agar to another portion of medium 1 was inoculated into the medium 1 in the above 500-ml Sakaguchi flask and cultivated at 34° C. for 10 hours. Thereafter, cells were harvested from the culture broth by centrifugation and washed with 0.05M tris-HCl (tris hydrochloride) buffer.

The cells of Nocardia opaca C-8-5 (1.5 g on the dry cell basis) as obtained in the above manner were suspended in 40 ml of 0.05M tris-HCl buffer (pH 7.8). The cell suspension was mixed with 40 ml of 4% (by weight) aqueous sodium alginate solution and the mixture was added dropwise to 0.5M aqueous calcium chloride solution to thereby shape the mixture into beads (about 3 mm in diameter). A 0.7-cm$^3$ portion of the thus-obtained beads containing immobilized cells of *Nocardia opaca* C-8-5 (containing 12 mg of the cells on the dry cell basis) was immersed in 10 ml of medium 1 at 37° C. for 36 hours and then washed with 0.05M tris-HCl buffer (pH 7.8).

Phenylpyruvic acid was added to 0.05M tris-HCl buffer (pH 7.8) to a concentration of 10 millimoles per liter, followed by addition of ammonium chloride to a concentration of 0.2 mole per liter. After admixing, 10 ml of the solution thus obtained was placed, together with the beads obtained above, in a 50-ml stainless steel autoclave reactor. After substitution of the atmosphere within the reactor with hydrogen gas, the reactor was pressurized to 100 atmospheres (absolute) with hydrogen gas. While maintaining the hydrogen gas pressure at 100 atmospheres (absolute) and the reaction temperature at 37° C., the reaction was conducted for 10 hours. After completion of the reaction, the reaction mixture was subjected to bioassay and high-performance liquid chromatography. It was found that 1.4 mg of phenylpyruvic acid remained and that the yield of L-phenylalanine amounted to 12.8 mg. The rate of formation of L-phenylalanine was 10.8 micromoles/minute/gram (dry cell). The yield of L-phenylalanine was 78% based on the used phenylpyruvic acid and the selectivity to L-phenylalanine was 85%.

EXAMPLE 2

L-Phenylalanine was produced by following the procedure of Example 1 (1st reaction run). Thereafter, the cell-containing beads were recovered, immersed in 10 ml of medium 1 at 37° C. for 14 hours and then washed with 0.05M tris-HCl buffer (pH 7.8). The reaction procedure of Example 1 was again followed except that the beads so recovered and treated were used, to thereby produce L-phenylalanine (2nd reaction run). Thereafter, the serial procedure comprising recovering and treating the beads in the same manner as above and using the same in the reaction step was repeated for the production of L-phenylalanine (3rd, 4th and 5th reaction runs). The results obtained in the respective reaction runs are shown in Table 2.

TABLE 2

| Reaction run | 1st | 2nd | 3rd | 4th | 5th |
| --- | --- | --- | --- | --- | --- |
| Residual phenylpyruvic acid (mg) | 1.4 | 0.6 | 1.1 | 2.8 | 3.0 |
| L-Phenylalanine formed (mg) | 12.8 | 13.7 | 13.1 | 11.6 | 11.3 |
| Rate of formation of L-phenylalanine [micromoles/minute/g (dry cells)] | 10.8 | 11.5 | 11.0 | 9.8 | 9.5 |
| Yield of L-phenylalanine based on the used phenylpyruvic acid (%) | 78 | 83 | 79 | 70 | 68 |
| Selectivity to L-phenylalanine (%) | 85 | 86 | 85 | 85 | 84 |

EXAMPLE 3

The whole procedure of Example 2 was repeated except that the beads recovered after each reaction run were immersed, at 37° C. for 14 hours, in 10 ml of an aqueous solution prepared by adding L-phenylalanine to 0.1M tris-HCl buffer (pH 8.0) to a concentration of 0.3% by weight. The results obtained are shown in Table 3.

TABLE 3

| Reaction run | 1st | 2nd | 3rd | 4th | 5th |
| --- | --- | --- | --- | --- | --- |
| Residual phenylpyruvic acid (mg) | 1.4 | 2.0 | 3.1 | 4.1 | 4.3 |
| L-Phenylalanine formed (mg) | 12.8 | 12.5 | 11.4 | 10.4 | 10.2 |
| Rate of formation of L-phenylalanine [micromoles/minute/g (dry cells)] | 10.8 | 10.5 | 9.6 | 8.8 | 8.6 |
| Yield of L-phenylalanine based on the used phenylpyruvic acid (%) | 78 | 76 | 69 | 63 | 62 |
| Selectivity to L-phenylalanine (%) | 85 | 86 | 85 | 84 | 84 |

EXAMPLE 4

L-Phenylalanine was produced by following the same procedure as described in Example 1 (1st reaction run). Thereafter, the cell-containing beads were recovered and washed with 0.05M tris-HCl buffer (pH 7.8). The reaction procedure of Example 1 was again followed except that the beads thus recovered and treated were used, to thereby produce L-phenylalanine (2nd reaction run). The results obtained in each run are shown in Table 4.

TABLE 4

| Reaction run | 1st | 2nd |
| --- | --- | --- |
| Residual phenylpyruvic acid (mg) | 1.4 | 3.0 |
| L-Phenylalanine formed (mg) | 12.8 | 11.3 |
| Rate of formation of L-phenylalanine [micromoles/minute/g (dry cells)] | 10.8 | 9.5 |
| Yield of L-phenylalanine based on the used phenylpyruvic acid (%) | 78 | 68 |
| Selectivity to L-phenylalanine (%) | 85 | 84 |

EXAMPLE 5

The procedure of Example 1 was followed except that 5.3 mg of NADH was added to the reaction system and that the reaction period was 5 hours. The reaction mixture thus obtained contained 9.0 mg of phenylpyruvic acid and 6.9 mg of L-phenylalanine. The rate of formation of L-phenylalanine was 11.7 micromoles/minute/gram (dry cells). The yield of L-phenylalanine was 42% based on the used phenylpyruvic acid and the selectivity to L-phenylalanine was 93%.

EXAMPLE 6

The procedure of Example 1 was followed with modifications such that 1.5 cm$^3$ of the beads obtained by immobilizing cells of *Nocardia opaca* C-8-5, which contained 25 mg of cells on the dry cell basis, were used without immersing in medium 1 and that the initial ammonium chloride concentration in the aqueous solution in the reaction system was not 0.2 mole per liter but 0.5 mole per liter. The reaction mixture thus obtained contained 2.8 mg of phenylpyruvic acid and 10.9 mg of L-phenylalanine. The rate of formation of L-phenylalanine was 4.4 micromoles/minute/gram (dry cells). The yield of L-phenylalanine was 66% based on the used phenylpyruvic acid and the selectivity to L-phenylalanine was 80%.

EXAMPLE 7

Meat extract (0.5 g), 0.5 g of peptone, 0.5 g of sodium chloride and 0.3 g of phenylpyruvic acid were dissolved in purified water, the solution was adjusted to pH 7.2 by adding 1N aqueous sodium hydroxide and the volume was made 100 ml by further adding purified water. A 50-ml portion of the medium thus prepared was placed in a 500-ml Sakaguchi flask, steam-sterilized at 110° C. for 10 minutes, and inoculated with the strain *Nocardia opaca* C-8-5. Cultivation was conducted at 34° C. for 15 hours and, thereafter, cells were harvested by centrifugation and washed with isotonic sodium chloride solution.

The thus-obtained cells of *Nocardia opaca* C-8-5 (1.5 g on the dry cell basis) were suspended in 50 ml of 0.2M tris-HCl buffer (pH 7.8). This cell suspension was mixed with 50 ml of 4% (by weight) aqueous sodium alginate solution and the mixture was added dropwise to 0.1M aqueous calcium chloride solution, whereby beads (about 3 mm in diameter) were formed. A 25-ml stainless steel autoclave reactor was charged with a 1.5-cm$^3$ portion of the beads obtained with the cells of Nocardia opaca C-8-5 being immobilized therein (said portion containing 30 mg of cells on the dry cell basis), 0.5 ml of 0.1M aqueous phenylpyruvic acid solution, 1 ml of 1M aqueous ammonium chloride solution, 0.66 mg of NAD and 3.5 ml of 0.2M tris-HCl buffer (pH 7.8) and, after substitution of the atmosphere within the reactor with hydrogen gas, pressurized to 100 atmospheres (absolute) with hydrogen gas. While maintaining the hydrogen gas pressure at 100 atmospheres (absolute) and the reaction temperature at 37° C., the reaction was conducted for 10 hours. The yield of L-phenylalanine was 1.6 mg. The rate of formation of L-phenylalanine was 0.55 micromole/minute/gram (dry cells) and the yield of L-phenylalanine was 19% based on the used phenylpyruvic acid.

EXAMPLE 8

The cultivation, cell immobilization and reaction procedure of Example 7 was followed except that NAD was not added to the reaction system. The yield of L-phenylalanine was 1.1 mg. The rate of formation of L-phenylalanine was 0.36 micromole/minute/gram (dry cells) and the yield of L-phenylalanine was 13% based on the used phenylpyruvic acid.

EXAMPLE 9

The cultivation, cell immobilization and reaction procedure of Example 7 was followed except that 0.66 mg of NADH was used in lieu of NAD. The yield of L-phenylalanine was 1.8 mg. The rate of formation of L-phenylalanine was 0.60 micromole/minute/gram (dry cells) and the yield of L-phenylalanine was 22% based on the used phenylpyruvic acid.

EXAMPLE 10

The cultivation, cell immobilization and reaction procedure of Example 7 was followed except that the strain *Nocardia coeliaca* C-7-5 was used in lieu of the strain *Nocardia opaca* C-8-5. The yield of L-phenylalanine was 1.2 mg. The rate of formation of L-phenylalanine was 0.40 micromole/minute/gram (dry cells) and the yield of L-phenylalanine was 15% based on the used phenylpyruvic acid.

EXAMPLE 11

The cultivation, cell immobilization and reaction procedure of Example 7 was followed except that the strain *Nocardia erythropolis* C-6-2 was used in lieu of the strain *Nocardia opaca* C-8-5. The yield of L-phenylalanine was 1.4 mg. The rate of formation of L-phenylalanine was 0.48 micromole/minute/gram (dry cells) and the yield of L-phenylalanine was 17% based on the used phenylpyruvic acid.

EXAMPLE 12

Using the cells (30 mg on the dry cell basis) obtained by following the cultivation procedure of Example 8 directly in the reaction step without immobilization, the L-phenylalanine formation reaction was carried out in the same manner as in Example 8. The yield of L-phenylalanine was 2.4 mg. The rate of formation of L-phenylalanine was 0.80 micromole/minute/gram (dry cells) and the yield of L-phenylalanine was 29% based on the used phenylpyruvic acid.

EXAMPLE 13

The cells (1.5 g on the dry cell basis) obtained by following the cultivation procedure of Example 7 were suspended in 50 ml of 0.1M phosphate buffer (pH 7.8). The cell suspension was mixed with 50 ml of 4% (by weight) aqueous agar solution and the mixture was allowed to coagulate while cooling at 0° C. The solid mass was cut to pieces (cubes about 5×5×5 mm in size) and the pieces were stored in 0.1M phosphate buffer (pH 7.8).

The L-phenylalanine formation reaction was conducted in the same manner as in Example 8 except that the immobilized cells obtained in the above manner were used. The yield of L-phenylalanine was 1.0 mg. The rate of formation of L-phenylalanine was 0.35 micromole/minute/gram (dry cells) and the yield of L-phenylalanine was 12% based on the used phenylpyruvic acid.

EXAMPLES 14–16

The cultivation, cell immobilization and reaction procedure of Example 8 was followed except that 1 ml of an aqueous solution containing the amino group donor specified in Table 5 in a concentration of 1 mole per liter (Examples 14 and 16) or 0.5 mole per liter (Example 15) was added to the reaction system in lieu of 1 ml of 1M aqueous ammonium chloride. The results obtained are shown in Table 5.

TABLE 5

| Example No. | Amino group donor | Yield of L-phenyl-alanine (mg) | Rate of formation of L-phenylalanine [micromoles/min/g (dry cells)] | Yield of L-phenyl-alanine based on the used phenyl-pyruvic acid (%) |
|---|---|---|---|---|
| 14 | Ammonium acetate | 1.1 | 0.37 | 13 |
| 15 | Ammonium sulfate | 1.0 | 0.34 | 12 |
| 16 | Ammonia | 1.0 | 0.33 | 12 |

EXAMPLES 17 & 18

The cultivation, cell immobilization and reaction were carried out in the same manner as in Example 8 except that the hydrogen gas pressure was 1 atmosphere (absolute) or 50 atmospheres (absolute) and that the reaction period was 7 hours. The results obtained are shown in Table 6.

TABLE 6

| Example No. | Hydrogen gas pressure [atm (abs)] | Yield of L-phenyl-alanine (mg) | Rate of formation of L-phenylalanine [micromoles/min/g (dry cells)] | Yield of L-phenyl-alanine based on the used phenyl-pyruvic acid (%) |
|---|---|---|---|---|
| 17 | 1 | 0.23 | 0.11 | 2.8 |
| 18 | 50 | 0.42 | 0.20 | 5.1 |

What is claimed is:

1. A process for producing L-phenylalanine which comprises immobilizing a microorganism selected from the group consisting of the strains *Nocardia opaca*, C-8-5, FERM BP-1119, *Nocardia coeliaca* C-7-5, FERM BP-1117, and *Nocardia erythropolis* C-6-2, FERM BP-1118 to a solid support and contacting said immobilized microorganism with an aqueous solution containing phenylpyruvic acid or a salt thereof and an amino group donor selected from the group consisting of an ammonium salt and ammonia in a hydrogen gas atmosphere wherein the hydrogen gas atmosphere is 50 to 200 atmospheres, and wherein said contacting is effected under conditions which result in the production and accumulation of L-phenylalanine in the aqueous solution, and recovering the produced L-phenylalanine.

2. The process of claim 1, wherein the microorganism is the strain *Nocardia opaca* C-8-5 FERM BP-1119.

3. The process of claim 1, wherein the microorganism is the strain *Nocardia coeliaca* C-7-5 FERM BP-1117.

4. The process of claim 1, wherein the microorganism is the strain *Nocardia erythropolis* C-6-2 FERM BP-1118.

5. The process of claim 1, wherein at least one coenzyme selected from the group consisting of nicotinamide-adenine dinucleotide and reduced nicotinamide-adenine dinucleotide is added to the aqueous solution.

6. The process of claim 1 wherein L-phenylalanine is recovered by removing the immobilized microorganism from the aqueous solution containing L-phenylalanine and recovering the L-phenylalanine from said aqueous solution.

7. The process of claim 1 wherein after L-phenylalanine has been produced, the immobilized microorganism cells are removed from the aqueous solution and the L-phenylalanine producing process is repeated by contacting said removed immobilized microorganism with a second aqueous solution containing phenylpyruvic acid or a salt thereof and an amino group donor selected from the group consisting of an ammonium salt and ammonia in a hydrogen gas atmosphere wherein the hydrogen gas atmosphere is 50 to 200 atmospheres, and wherein said contacting is effected under conditions which result in the production and accumulation of L-phenylalanine in the second aqueous solution and wherein the produced L-phenylalanine is recovered from said second aqueous solution.

8. The process of claim 1 wherein the immobilized microorganism is separated from the aqueous solution prior to recovery of L-phenylalanine by filtering or centrifuging the immobilized microorganism from the aqueous solution containing L-phenylalanine.

9. The process of claim 1 wherein L-phenylalanine is recovered from the aqueous solution by a process including ion exchange or crystallization.

10. A process for producing L-phenylalanine which comprises immobilizing a microorganism selected from the group consisting of the strains *Nocardia opaca*, C-8-5, FERM BP-1119, *Nocardia coeliaca* C-7-5, FERM BP-1117, and *Nocardia erythropolis* C-6-2, FERM BP-1112, to a solid support and contacting said immobilized microorganism with an aqueous solution containing phenylpyruvic acid or a salt thereof and an amino group donor selected from the group consisting of ammonium salts and ammonia in a hydrogen gas atmosphere wherein the hydrogen gas atmosphere is 100 to 200 atmospheres, and wherein said contacting is effected under conditions which result in the production and accumulation of L-phenylalanine in the aqueous solution, and recovering the produced L-phenylalanine.

11. The process of claim 1 wherein L-phenylalanine is recovered by removing the immobilized microorganism from the aqueous solution and recovering the L-phenylalanine from the aqueous solution.

12. The process of claim 10 wherein after L-phenylalanine has been produced, the immobilized microorganism is removed from the aqueous solution and the L-phenylalanine producing process is repeated by contacting said removed immobilized microorganism with a second aqueous solution containing phenylpyruvic acid or a salt thereof and an amino group donor selected from the group consisting of an ammonium salt and ammonia in a hydrogen gas atmosphere wherein the hydrogen gas atmosphere is 100 to 200 atmospheres, and wherein said contacting is effected under conditions which result in the production and accumulation of L-phenylalanine the aqueous solution and wherein the produced L-phenylalanine is recovered from second aqueous solution.

13. The process of claim 10 wherein the immobilized microorganism is separated from the aqueous solution prior to recovery of L-phenylalanine by filtering or centrifuging the immobilized microorganism from the aqueous solution containing L-phenylalanine.

14. The process of claim 10 wherein the L-phenylalanine is recovered from the aqueous solution by a process including ion exchange or crystallization.

* * * * *